US009926194B2

(12) United States Patent
Panchapakesan

(10) Patent No.: US 9,926,194 B2
(45) Date of Patent: Mar. 27, 2018

(54) METHOD AND DEVICE FOR DETECTING CELLULAR TARGETS IN BODILY SOURCES USING CARBON NANOTUBE THIN FILM

(75) Inventor: Balaji Panchapakesan, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 1669 days.

(21) Appl. No.: 13/045,135

(22) Filed: Mar. 10, 2011

(65) Prior Publication Data

US 2011/0224091 A1 Sep. 15, 2011

Related U.S. Application Data

(60) Provisional application No. 61/312,913, filed on Mar. 11, 2010.

(51) Int. Cl.
| | | |
|---|---|---|
| B82Y 15/00 | (2011.01) | |
| B82Y 30/00 | (2011.01) | |
| G01N 27/414 | (2006.01) | |

(52) U.S. Cl.
CPC ............ B82Y 15/00 (2013.01); B82Y 30/00 (2013.01); G01N 27/4145 (2013.01); G01N 27/4146 (2013.01); Y10T 156/1039 (2015.01)

(58) Field of Classification Search
None
See application file for complete search history.

(56) References Cited

U.S. PATENT DOCUMENTS

| | | |
|---|---|---|
| 2006/0040318 A1 | 2/2006 | Melker et al. |
| 2006/0273356 A1* | 12/2006 | Matsumoto ............ B82Y 10/00 257/253 |
| 2008/0160539 A1 | 7/2008 | Murphy et al. |
| 2009/0004670 A1 | 1/2009 | Zhang et al. |
| 2009/0072161 A1 | 3/2009 | Ben-Yakar et al. |
| 2009/0220382 A1 | 9/2009 | Palena et al. |
| 2009/0326520 A1 | 12/2009 | Lee et al. |

FOREIGN PATENT DOCUMENTS

| | | |
|---|---|---|
| WO | WO2008082374 | 7/2008 |
| WO | WO2009/016389 A1 | 2/2009 |

OTHER PUBLICATIONS

Zheng et al (2005 Nature Biotechnology 23:1294-1301).*
Panchapakesan, B. et al., "Single-Wall Carbon Nanotubes with Adsorbed Antibodies Detect Live Breast Cancer Cells," NanoBiotechnology, vol. 1, 2005, pp. 353-360.
Shao, N. et al., "Nanotube-antibody biosensor arrays for the detection of circulating breast cancer cells," Nanotechnology vol. 19, 465101, 2008, 11 pages.
Ferrari, M., "Cancer Nanotechnology: Opportunities and Challenges," Nature Rev. Cancer, vol. 5, pp. 161-171, Mar. 2005.
Teker, Kasif; Wickstrom, Eric; Panchapakesan, Balaji , Biomolecular tuning of electronic transport properties of carbon nanotubes via antibody functionalization, IEEE Sensors Journal vol. 6 Issue: 6 pp. 1422-1428 DOI: 10.1109/JSEN.2006.884564 Published: Dec. 2006.
Liu, Zhuang; Tabakman, Scott; Welsher, Kevin; Dai, Hongjie , Carbon Nanotubes in Biology and Medicine: In vitro and in vivo Detection, Imaging and Drug Delivery , Nano Research vol. 2 Issue: 2 pp. 85-120 DOI: 10.1007/s12274-009-9009-8 Published: Feb. 2009.
Xiao, Yan; Gao, Xiugong; Taratula, Oleh; Treado, Stephen; Urbas, Aaron; Holbrook, R. David; Cavicchi, Richard E.; Avedisian, C. Thomas; Mitra, Somenath; Savla, Ronak; Wagner, Paul D.; Srivastava, Sudhir; He, Huixin , Anti-HER2 IgY antibody-functionalized single-walled carbon nanotubes for detection and selective destruction of breast cancer cells , BMC Cancer vol. 9 Article No. 351 DOI: 10.1186/1471-2407-9-351 Published: Oct. 2, 2009.
Ou, Zhongmin; Wu, Baoyan; Xing, Da; Zhou, Feifan; Wang, Huiying; Tang, Yonghong, Functional single-walled carbon nanotubes based on an integrin alpha(v)beta(3) monoclonal antibody for highly efficient cancer cell targeting, Nanotechnology vol. 20 Issue: 10 Article No. 105102 DOI: 10.1088/0957-4484/20/10/105102 Published: Mar. 11, 2009.
Menard-Moyon, Cecilia; Kostarelos, Kostas; Prato, Maurizio; Bianco, Alberto, Functionalized Carbon Nanotubes for Probing and Modulating Molecular Functions , Chemistry & Biology vol. 17 Issue: 2 pp. 107-115 DOI: 10.1016/j.chembiol.2010.01.009 Published: Feb. 26, 2010.
Liu, Fei; Choi, Ki Seok; Park, Tae Jung; Lee, Sang Yup; Seo, Tae Seok, Graphene-based electrochemical biosensor for pathogenic virus detection, Biochip Journal vol. 5 Issue: 2 pp. 123-128 DOI: 10.1007/s13206-011-5204-2 Published: Jun. 20, 2011.
International Preliminary Report on Patentability, Written Opinion of the International Search Authority Search for Application No. PCT/US2011/028050, dated Sep. 11, 2012.
Byon H. R. et al.: "Network Single-Walled Carbon Nanotube-Field Effect Transistors (SWNT-FETs) with Increased Schottky Contact Area for Highly Sensitive Biosensor Applications," J. Am. Chemical Soc., vol. 128, No. 7, Jan. 31, 2006, pp. 2188-2189.

(Continued)

Primary Examiner — Christopher M Gross
(74) Attorney, Agent, or Firm — Wood Herron & Evans LLP

(57) ABSTRACT

A device and method detect cellular targets in a bodily source by utilizing a biofunctional pad comprised of a thin film of carbon nanotubes (CNT's). When antibodies are absorbed by the CNT's, cellular targets having markers matching the antibodies may be detected in a bodily source placed upon the biofunctional pad by measuring the conductivity of the thin film using conductive contacts electrically coupled to the thin film, as the binding of the receptors in the cellular targets to the antibodies changes the free energy in the thin film. In many respects, the device functions as a Field Effect Transistor (FET) with the bodily source, e.g., blood, acting as a polyelectrolyte liquid gate electrode to create a varying electrostatic charge or capacitance in the thin film based upon the binding of cellular targets in the source to the antibodies present on the biofunctional pad.

20 Claims, 10 Drawing Sheets

(56) References Cited

OTHER PUBLICATIONS

Chen R. J. et al.: "An Investigation of the Mechanisms of Electronic Sensing of Protein Adsorption on Carbon Nanotube Devices," J. Am Chem. Soc., vol. 126, No. 5, Jan. 15, 2004, pp. 1563-1568.
Allen B. L. et al.: "Carbon Nanotube Field-Effect-Transistor-Based Biosensors," Adv. Mater., vol. 19, No. 11, Jun. 4, 2007, pp. 1439-1451.
Star A. et al.: "Label-free Detection of DNA Hybridization Using Carbon Nanotube Network Field-effect Transistors," Proceedings of the National Academy of Sciences, National Academy of Scienses, Washington, D.C., US, vol. 103, No. 4, Jan. 24, 2006, pp. 921-926.
International Search Report for Application No. PCT/US2011/028050, dated Jun. 9, 2011.

* cited by examiner

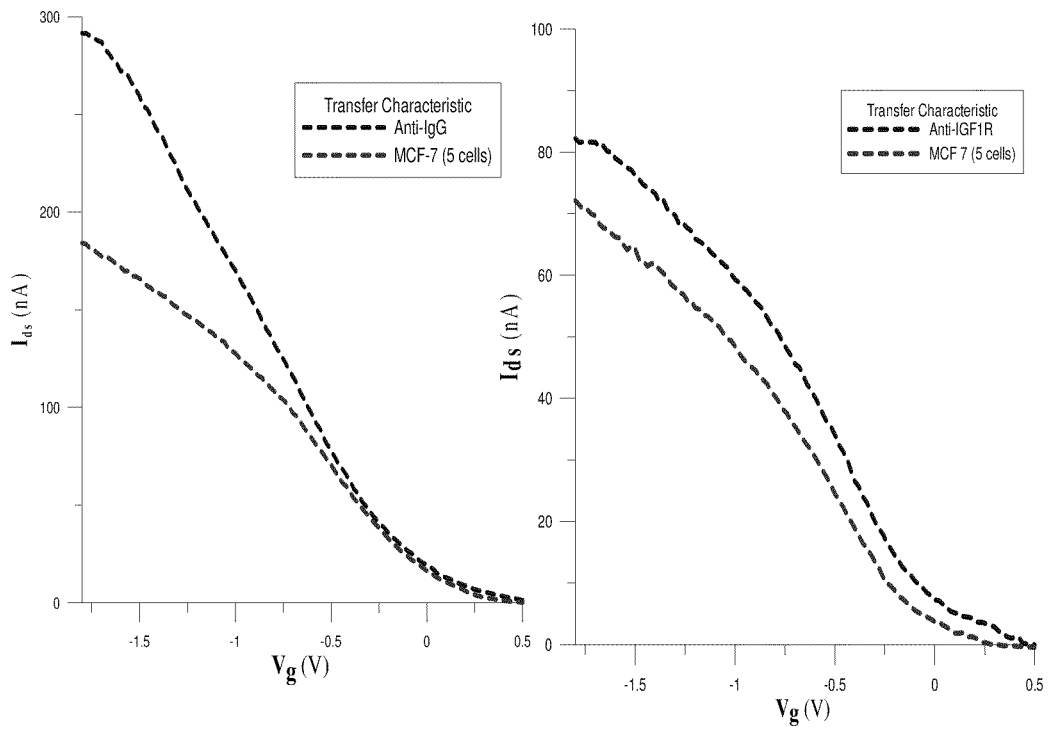
FIG. 15A  FIG. 15B
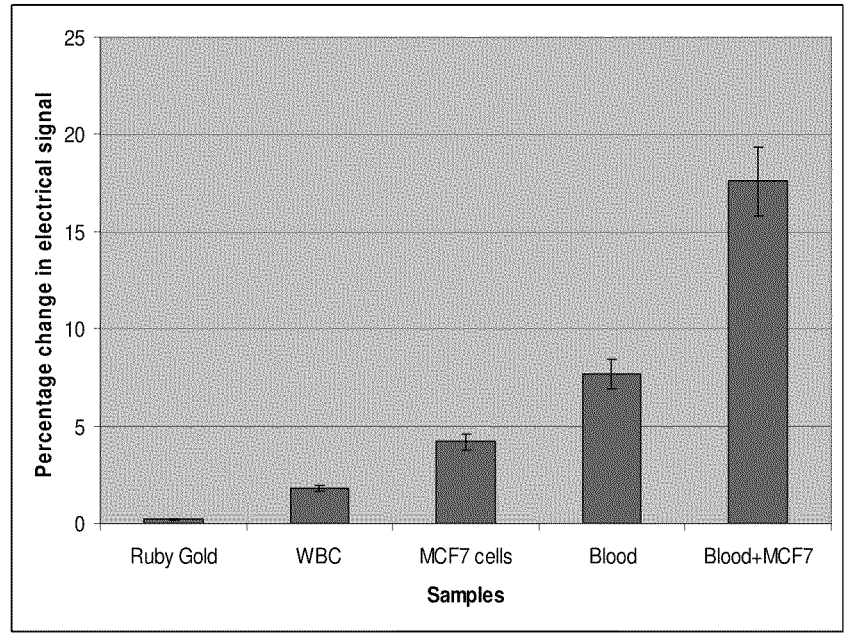
FIG. 16

METHOD AND DEVICE FOR DETECTING CELLULAR TARGETS IN BODILY SOURCES USING CARBON NANOTUBE THIN FILM

CROSS-REFERENCE TO RELATED APPLICATIONS

This application claims priority to U.S. Provisional Application Ser. No. 61/312,913 filed by Balaji Panchapakesan on Mar. 11, 2010, and entitled "METHOD AND DEVICE FOR DETECTING CELLULAR TARGETS IN BODILY SOURCES USING CARBON NANOTUBE THIN FILM," which application is incorporated by reference in its entirety.

GOVERNMENT RIGHTS

This invention was made with Government support under Grant No. ECCS 0853066 awarded by the National Science Foundation. The Government has certain rights in this invention.

FIELD OF THE INVENTION

The invention is generally related to detecting cellular targets in bodily sources, e.g., detecting circulating cancer cells in blood. The invention is also generally related to the use of carbon nanotubes (CNT's) in medical diagnostic applications.

BACKGROUND OF THE INVENTION

Identification and quantitation of numerous biological molecules to generate a complex molecular profile is required for diagnosis, monitoring, and prognostic evaluation of complex diseases such as cancer. Despite outstanding progress in the area of cancer biology, significant challenges remain in translating biological knowledge of cancer surface markers into clinically relevant devices that could be used as diagnostic or monitoring tools for cancer management. Developing high-throughput and low cost diagnostic cell and tissue analysis for disease detection has remained a challenge.

For example, breast cancer is the most diagnosed cancer in women, and it has been found that developing breast cancers shed transformed cells into the blood, with more malignant breast cancer cells appearing in the blood in later stages. It is believed by many that early detection of circulating breast cancer cells might improve diagnosis of early breast cancer and ultimately reduce breast cancer-related deaths. Therefore, significant efforts have been made toward the development of methods and devices for detecting circulating breast cancer cells in blood.

Circulating tumor cells (CTC's) have long been analyzed ex vivo by flow cytometry and fluorescence microscopy to measure characteristic cell surface markers, such as epithelial cell adhesion marker (EpCAM), a general purpose epithelial cell marker that is common to circulating tumor cells. Many of these techniques, however, are expensive and time consuming, often requiring several days to generate results.

More recently, it has been found that small bundles of single wall carbon nanotubes (SWCNT), ~10 nm diameter, lithographically patterned between two electrodes, with adsorbed monoclonal antibodies, will display a sensitivity to a single cancer cell in 1 μL of blood. Moreover, such devices have the potential to detect the presence of cancer cells in blood in a matter of minutes, rather than days as is often the case with other methodologies. However, the use of single or small bundles of SWCNT's presents challenges in a clinical setting due to the difficulty in fabricating such single or small bundle SWCNT samples, and ensuring that the cancer cells are bridging the electrodes to achieve reliable detection. Furthermore, the use of nanoscale devices precludes the use of large blood volumes that are typically analyzed in a clinical setting.

Therefore, a need continues to exist in the art for an improved methodology and device for detecting cancer cells and other cellular targets in blood and other bodily sources.

SUMMARY OF THE INVENTION

The invention addresses these and other problems associated with the prior art by providing a device and method of detecting cellular targets in a bodily source utilizing a biofunctional pad comprised of a thin film of carbon nanotubes (CNT's). When antibodies are absorbed by the CNT's, cellular targets having markers matching the antibodies may be detected in a bodily source placed upon the biofunctional pad by measuring the conductivity of the thin film using conductive contacts electrically coupled to the thin film, as the binding of the receptors in the cellular targets to the antibodies changes the free energy in the thin film. In many respects, the device functions as a Field Effect Transistor (FET) with the bodily source, e.g., blood, acting as a polyelectrolyte liquid gate electrode to create a varying electrostatic charge or capacitance in the thin film based upon the binding of cellular targets in the source to the antibodies present on the biofunctional pad.

Consistent with one aspect of the invention, a device for detecting cellular targets in a bodily source includes a substrate; a biofunctional pad comprising a thin film of carbon nanotubes (CNT's) disposed on the substrate and adapted to receive antibodies associated with a cellular target; and a plurality of conductive contacts disposed on the substrate and electrically coupled to the thin film. The plurality of conductive contacts are configured for use in detecting the cellular target in a bodily source by measuring a conductivity of the thin film when the antibodies are received by the thin film and the bodily source is disposed on the biofunctional pad and in contact with the antibodies, whereby the conductivity of the thin film is indicative of the presence of the cellular target in the bodily source.

Consistent with another aspect of the invention, a method of fabricating a sensor for detecting cellular targets in a bodily source includes forming a thin film of carbon nanotubes (CNT's) on a carrier using vacuum filtration; mechanically bonding the thin film to a dielectric layer on a semiconductor substrate; separating the thin film from the carrier; patterning the thin film to form a biofunctional pad; and depositing a plurality of conductive contacts on the substrate, with at least a portion of each conductive contact overlapping and electrically coupled to the thin film.

Consistent with yet another aspect of the invention, a method of detecting cellular targets in a bodily source includes placing a bodily source on a biofunctional pad comprising a thin film of carbon nanotubes (CNT's) upon which is disposed antibodies associated with a cellular target; and measuring the conductivity of the thin film using a plurality of conductive contacts electrically coupled to the thin film, whereby the conductivity of the thin film is indicative of the presence of the cellular target in the bodily source.

These and other advantages and features, which characterize the invention, are set forth in the claims annexed hereto and forming a further part hereof. However, for a better understanding of the invention, and of the advantages and objectives attained through its use, reference should be made to the Drawings, and to the accompanying descriptive matter, in which there is described exemplary embodiments of the invention.

BRIEF DESCRIPTION OF THE DRAWINGS

FIGS. 15A and 15B are respective plots of I-Vg for anti-IgG and MCF7 cells interaction (FIG. 15A), and of I-Vg for anti-IGF1R and MCF7 cells interaction (FIG. 15B).

FIG. 16 is a bar graph illustrating percentage changes in an electrical signal applied across a CNT thin film for samples of samples of ruby gold nanoparticles, isolated white blood cells, isolated MCF7 cancer cells, blood and blood mixed with MCF7 cells.

DETAILED DESCRIPTION

Embodiments consistent with the invention use thin films of carbon nanotubes (CNT's) for detecting surface receptors or markers in cellular targets in bodily sources, e.g., cancer cells in blood. As will become more apparent below, when blood mixed with cancer cells is brought into contact with a thin film of CNT's that has been functionalized with monoclonal antibodies, the conductivity of the thin film changes, and typically does so in a manner that is directly related to the number of cancer cells in blood. Therefore, by applying a known voltage across the thin film, e.g., through a pair of conductive contacts or electrodes electrically coupled to the thin film, the presence of cancer cells can be determined from the current sensed through the film, with the current decreasing a function of the number of cells in the blood.

Among other benefits, the techniques described herein provide devices that are readily adaptable to clinical environments, and may have applicability in third world countries or in other instances where access to health care facilities is limited. Thin films of CNT's are readily adaptable to batch fabrication techniques and CMOS/MEMS fabrication techniques. In addition, as compared to conventional technologies, surface markers can be detected in blood in a few minutes vs. a few days, and the level of skill required of the technician may be substantially reduced.

One application of the invention, for breast cancer detection in blood, will hereinafter be the focus of the instant application. It will be appreciated by one of ordinary skill in the art that the invention may have applicability in connection with the detection of other forms of cancer, e.g., prostate cancer, or the detection of other cellular targets. In addition, the invention may have applicability in connection with detecting cellular targets in other bodily sources, e.g., other bodily fluids.

Figure 1:
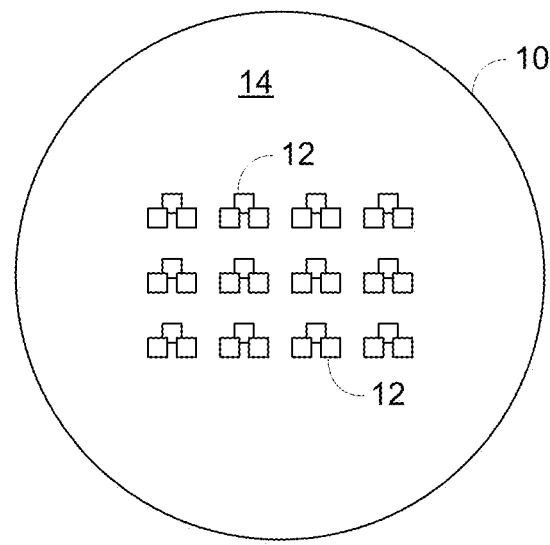
FIG. 1 is a top plan view of a cellular detection and profiling sensor array consistent with the invention.

Turning now to the Drawings, wherein like numbers denote like parts throughout the several views, FIG. 1 illustrates a device 10 consistent with the principles of the invention. Device 10 includes a sensor array of sensors 12 disposed on a substrate, e.g., a silicon or other semiconductor wafer 14. In the illustrated embodiment, each sensor 12 may be separately configured with different antibodies to target different cellular targets, and it may be desirable to provide multiple sensors 12 with the same antibodies, e.g., to provide the ability to double check results, or to test blood samples from different patients on the same device. While device 10 is illustrated with a 3×4 array of sensors 12, it will be appreciated that any number of sensors 12 may be disposed in a given device consistent with the invention. For example, it may be desirable in some embodiments to utilize 200 sensors 12 so that a 1 mL blood sample may be analyzed in 54 drops applied to the 200 sensors.

Figure 2:
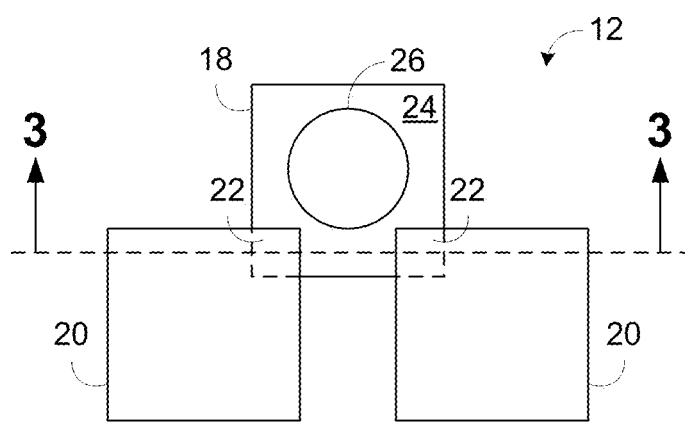
FIG. 2 is a top plan view of one of the sensors from the sensor array of FIG. 1.
Figure 3:
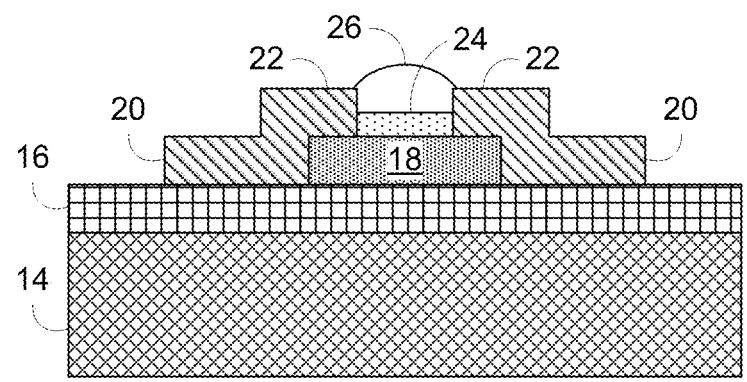
FIG. 3 is a cross-sectional view of the sensor of FIG. 2, taken along lines 3-3.

FIG. 2 illustrates one of sensors 12 in greater detail, while FIG. 3 illustrates a cross-section of one of sensors 12, taken along lines 3-3 of FIG. 2. Sensor 12 in the illustrated embodiment is formed on top of a dielectric layer 16 on substrate 16, e.g., a silicon dioxide layer. Sensor 12 includes a biofunctional pad 18 formed from a thin film of CNT's and a pair of contacts or electrodes 20 through which the conductivity of the thin film may be measured. Contacts 20 may be formed of gold or another conductive material, and partially overlap the thin film in regions 22.

In use, biofunctional pad 18 is functionalized to detect a particular marker on a cellular target by applying antibodies 24 on a surface thereof. Then, a drop of blood or other bodily source, illustrated at 26, is deposited on biofunctional pad 18, separated from contacts 20, and a voltage is applied across contacts 20 to generate a current that is measured to calculate the conductivity, i.e., the IV characteristics, of the thin film forming the biofunctional pad.

As noted above, each sensor 12 effectively functions as a Field Effect Transistor (FET) with the bodily source, e.g., blood, acting as a polyelectrolyte liquid gate electrode to create a varying electrostatic charge or capacitance in the thin film based upon the binding of cellular targets in the source to the antibodies present on the biofunctional pad.

As discussed in the aforementioned paper, CNT's are generally p-type materials, and as a result, applying a positive gate voltage to the thin film of CNT's depletes the carriers and reduces the overall conductance through the thin film. The dependence of conductance on gate voltage is ideal for biosensing applications, as the binding of charged species to the gate dielectric is analogous to applying a voltage through a gate electrode. Thus the conductance of a p-type CNT would decrease when a protein with a positive surface charge binds to an antibody. It has been found that blood spiked with cancer cells decreases or increases the conductance of the sensor with increasing number of cells depending on the net charge. This is a general pattern for many antibodies, although other antibodies, e.g., EGFR, may increase the conductance of the thin film with increasing number of cells. The mechanism is therefore one of electrostatic gating of the CNT thin film. It is believed that blood spiked with cancer cells acts as a gate electrode. Varying positive (negative) voltage at the gate electrode decreases (increases) the conductance of the device. In this case, increasing the number of cells is equivalent to increasing the voltage of the liquid gate. While this seems simplistic, one can also look at the capacitance of the liquid gate as a function of the Debye length to understand the reason for excellent gate coupling of blood with increase in cancer cells.

The total gate capacitance, which determines the charging of the CNT's under a certain gate voltage, consists of electrostatic (Ce) and quantum (Cq) components. For back-gating devices, the capacitance of the gate is given by $C_{bg}=2\pi\epsilon\epsilon_0/\ln(2h/r)$, where ($\epsilon\epsilon_0$) is the gate material dielectric constant (e.g., $3.9\times8.85\times10^{-12}$ F/m), h is the gate oxide thickness (e.g., 500 nm), and r is the thickness of the CNT film (e.g., 180 nm). The calculated capacitance per unit length of 500 nm silicon dioxide back gating is about $1.245\times10^{-10}$ F/m. For blood as a top gate one can approximate it as a liquid electrolyte top gate with a capacitance given by: $C_{liquid\ gate}=2\pi\epsilon\epsilon_0/\ln(r+\lambda_D/r)$, where $\lambda_D$ is the Debye length or the electronic screening length resulting from ions. Now if one assigns a value of ~10 nm for Debye length, the capacitance per unit length of the liquid gate is about $6.445\times10^{-8}$ F/m. Due to the higher capacitance, better gate channel coupling is achieved. Further, it can be seen that blood as a gate has a capacitance of two orders better than a conventional back gated structure. Although the Debye length varies with different salt concentrations, the estimated Debye length used in the calculation is still valid because the total capacitance variation caused by the change in the Debye length is small as long as it is still on the order of a few nanometers. Cell surface receptors with a net positive or negative charged increase or decrease the current in blood depending on their surface charge. Thus, by optimizing a sensor with thinner CNT films, one can achieve excellent gating in a liquid environment that can be used as a mechanism for sensing circulating cancer cells.

In addition, it is believed that change in current in a sensor consistent with the invention is also related to the extracellular and intra-cellular potentials of the cellular targets. This makes the sensor and method of its use highly specific for specific cell types.

It should also be noted that, after etching and patterning the thin film of CNT's, the surface of the thin film becomes highly hydrophobic due to the nature of the single walled CNT's (SWCNT's). The hydrophobic nature of the surface causes a deposited blood droplet to remain on a specific spot on the biofunctional pad without shorting the contacts. The hydrophobic nature of the surface also causes the antibodies to diffuse slowly and arrange themselves on the surface of the CNT's, and makes it possible for the adsorbed antibodies to interact with the cell surface antigens and create the change in conductivity.

Figure 4:
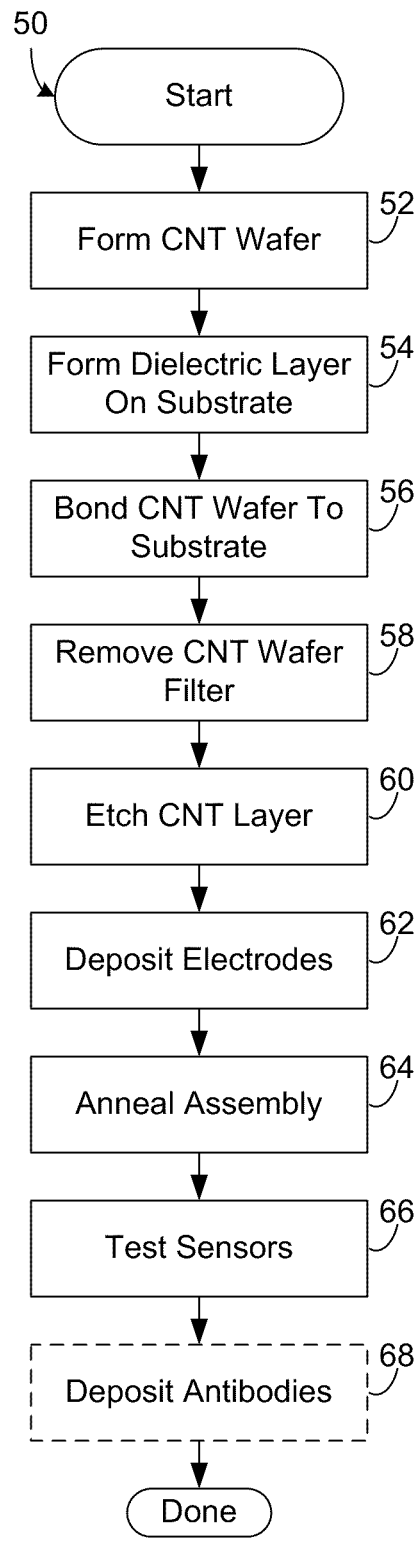
FIG. 4 is a flowchart illustrating exemplary steps in fabricating the sensor array of FIG. 1.
Figure 5A:
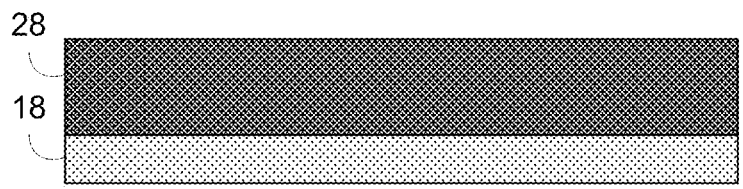
FIGS. 5A-5H are cross-sectional views illustrating the fabrication of the sensor array of FIG. 1 during various of the steps illustrated in FIG. 4.
Figure 5B:
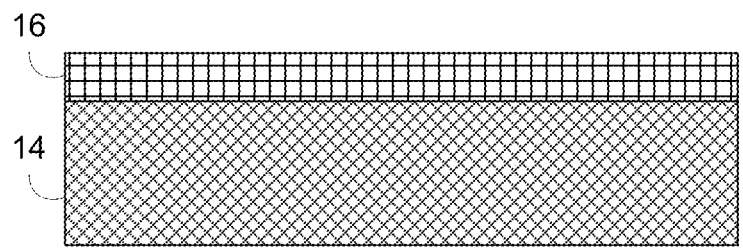

With additional reference to FIGS. 5A-5H, a sensor consistent with the invention may be fabricated using a process 50 shown in FIG. 4. Process 50 begins in block 52 by forming a CNT wafer, e.g., by a vacuum filtration technique such as disclosed in Lu et al., "Nanotube micro-optomechanical actuators," *Applied Physics Letters* 88, 253107 (2006). The wafer includes a thin film 18 of CNT's, e.g., about 100 nm to about 150 nm in thickness, deposited on a mixed cellulose ester (MCE) carrier or filter 28 (FIG. 5A).

Next, in block 54, the substrate is prepared by forming a dielectric layer 16 on a silicon or other semiconductor wafer 14 (FIG. 5B), e.g., through oxidation of the silicon wafer to create a layer of silicon dioxide.

Figure 5C:
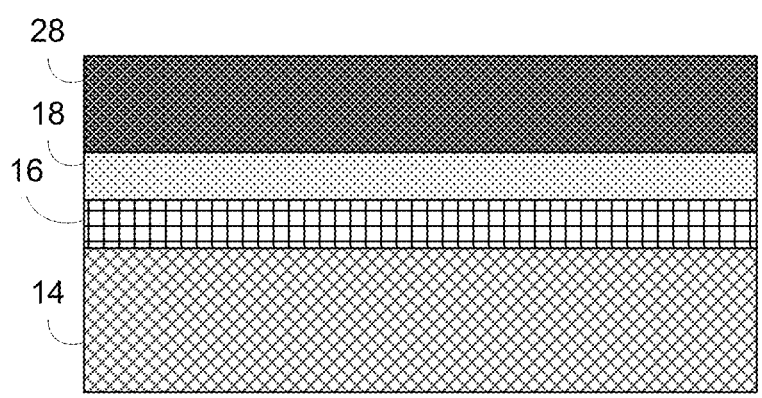
Figure 5D:
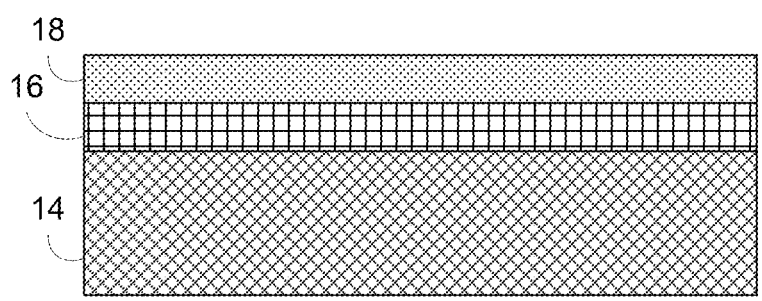

Next, in block 56, the CNT wafer is bonded to the substrate through mechanical compression while heating to about 75 degree Celsius, bonding thin film 18 to dielectric layer 16 (FIG. 5C). Thereafter, the CNT wafer filter 28 is removed in block 58 using an acetone vapor bath to dissolve the filter away from the thin film of CNT's (FIG. 5D).

Figure 5E:
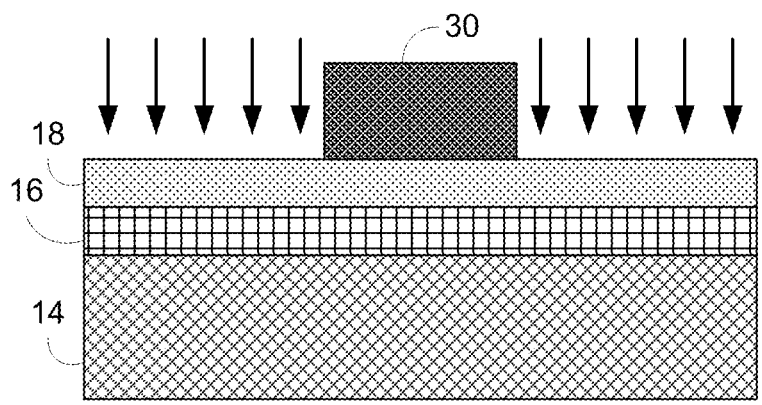
Figure 5F:
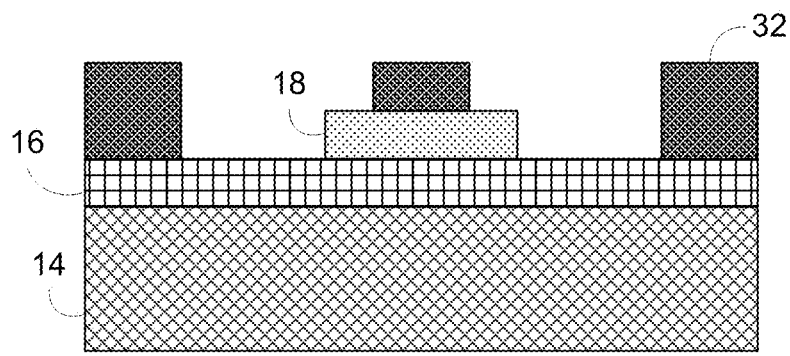

Next, in block 60, the CNT thin film is etched by patterning a photoresist mask 30 using a lithographic process to cover the regions of each biofunctional pad, and then etching the remaining CNT thin film using an etching technique such as deep reactive-ion etching (DRIE) (FIG. 5E). Thereafter, the photoresist mask is removed.

Figure 5G:
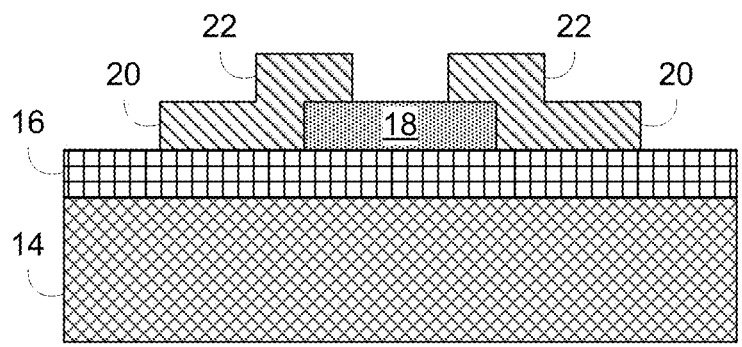

Next, in block 62, electrodes or contacts are deposited, first by patterning a photoresist mask 32 using a lithographic process to expose the regions of each contact (FIG. 5F) and then depositing a conductive material such as gold, aluminum, copper, platinum, or other conductive metal or alloy providing a low contact resistance, e.g., via sputtering or other suitable deposition technique. The contacts may be deposited, for example, to a thickness of about 100 nm. Thereafter, the photoresist mask is removed, resulting in contacts 20 being formed with overlapping regions 22 (FIG. 5G).

Next, in block 64, the assembly is annealed, e.g., at about 150 to about 200 degrees Celsius in an Argon or other inert gas atmosphere for about 20 minutes. Doing so improves the contact between each contact or electrode and the thin film, thereby lowering the contact resistance so that the bulk of the contact resistance in the sensor is due to the binding of cellular targets to the antibodies absorbed into the thin film of CNT's.

Next, in block 66, it may be desirable to test the sensors on the wafer, e.g., by measuring the IV characteristics of the sensors by applying a voltage across the contacts 20. In addition, Raman spectroscopy may be performed to characterize the CNT's in the thin film of each sensor and identify any potentially defective films.

Figure 5H:
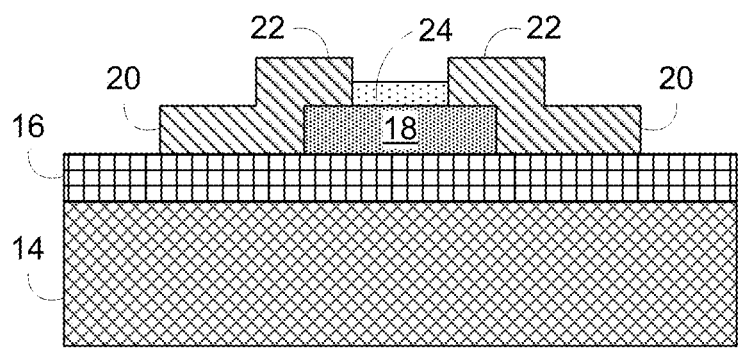

Subsequent to testing, it may also be desirable during fabrication, as shown in block 68, to deposit antibodies 24 on the biofunctional pad (FIG. 5H). Antibodies may be deposited, for example, via drop coating of pure antibodies, or via covalent bonding or other known techniques. In one suitable technique, antibodies may be drop coated onto a biofunctional pad and allowed to set for about 10 minutes to enable the antibodies to diffuse and be absorbed into the thin film, and then wash away the remaining liquid using deionized (DI) water. Depending upon the type of antibodies and the environmental robustness thereof, it may also be desirable to autoclave or freeze the sensors during the fabrication process to preserve the antibodies on the surface of the biofunctional pad until the sensors are ready to be used.

In an alternate embodiment, however, the sensors may be fabricated without antibodies deposited thereon, requiring the antibodies to be deposited immediately prior to use in a clinical environment.

In the embodiment illustrated in FIGS. 1-5H, each sensor includes a biofunctional pad 18 of about 1.5 mm×1.5 mm, with each contact 20 being about 1 mm×1 mm and overlapping the biofunctional pad in regions 22, sized about 0.1 mm×0.3 mm. In this embodiment, it may be desirable to drop coat about 5 µL to about 10 µL of antibodies at a concentration of about 5 µg/mL, which results in an about 20 nm thick layer of antibodies deposited on the biofunctional pad.

Figure 6:
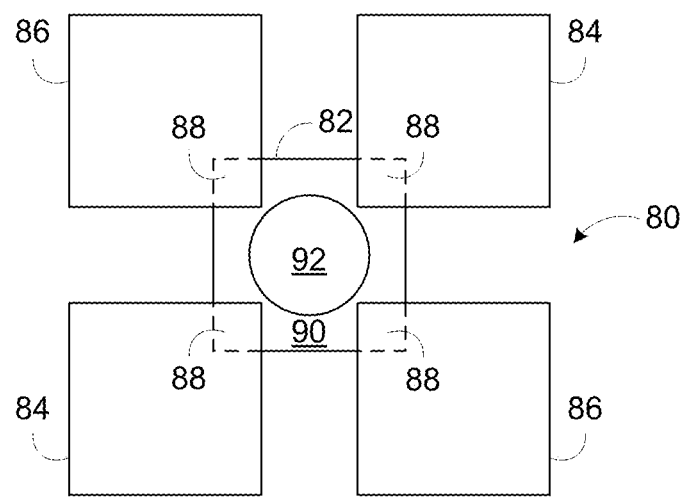
FIG. 6 is a top plan view of an alternate sensor to that of FIG. 2, incorporating separate drive and sensing contacts.

While a pair of contacts, disposed over two adjacent corners of the biofunctional pad, is used in each sensor 12, other configurations and numbers of contacts may be used in a sensor consistent with the invention. For example, FIG. 6 illustrates an alternate sensor 80 including a thin layer of CNT's 82 and four contacts 84, 86 overlapping in regions 88. One pair of contacts 84 disposed on opposite corners of biofunctional pad 82 may be used as drive pads, through which a current is passed, and the other pair of contacts 86 may be used as sensing pads, through which the resistance or conductivity of the biofunctional pad is measured. In other embodiments, contacts may be disposed in other positions, e.g., overlapping the edges, of a biofunctional pad.

Figure 7:
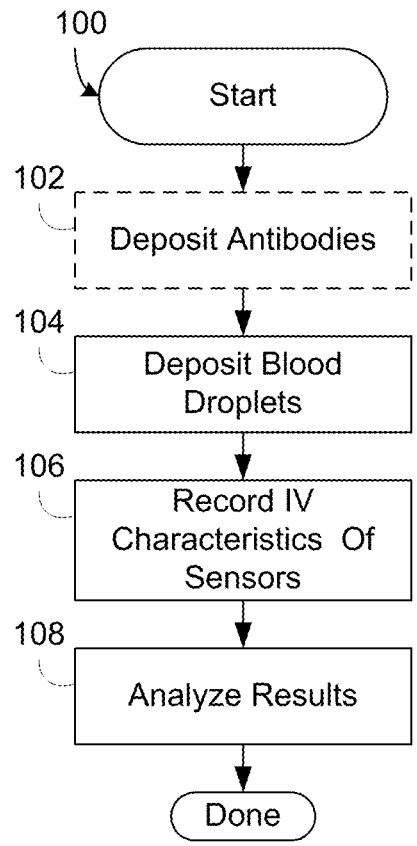
FIG. 7 is a flowchart illustrating exemplary steps in detecting and profiling cellular targets using the sensor array of FIG. 1.

FIG. 7 next illustrates a process 100 for testing a blood sample using device 10 of FIG. 1. Process 100 begins in block 102 by optionally depositing the antibodies on the biofunctional pads in the manner discussed above, if not already so done during fabrication. Next, in block 104, blood droplets (e.g., about 5 µL) are deposited on the biofunctional pads, without contacting the contacts, either manually or via a robotic system. Then, in block 106, the IV characteristics of the sensor are recorded over time by applying a known voltage, e.g., up to about 25 mV across the contacts thereof and measuring the current. In many instances, each sensor will stabilize within several minutes, e.g., 5 minutes or so, once all cellular targets in the blood bind with the antibodies. Thereafter, in block 108, the results may be analyzed to determine what cellular targets were found in the blood based upon what markers were expressed with the different antibodies on different sensors in the array. In addition, it may also be possible to predict or determine the number of cellular targets within each blood sample, e.g., the number of cancer cells predicted in a given drop of blood, as the IV characteristics of each sensor will change based upon the number of cells, and thus the number of bindings that occur with the antibodies.

The types of antibodies used to test a given blood sample may be different in different embodiments and applications. For example, to test for the presence of breast cancer, it may be desirable to utilize IGF1R, Her2, EpCAM, and EGFR antibodies on different sensors, while to test for the presence of prostate cancer, it may be desirable to utilize PSMA antibodies. It may even be desirable to utilize antibodies that express for different types of cancer on the same sensor array so that a single blood sample may be tested for the presence of multiple types of cancer. Other combinations of antibodies may also be used for other diagnostic applications of the invention.

Figure 8:
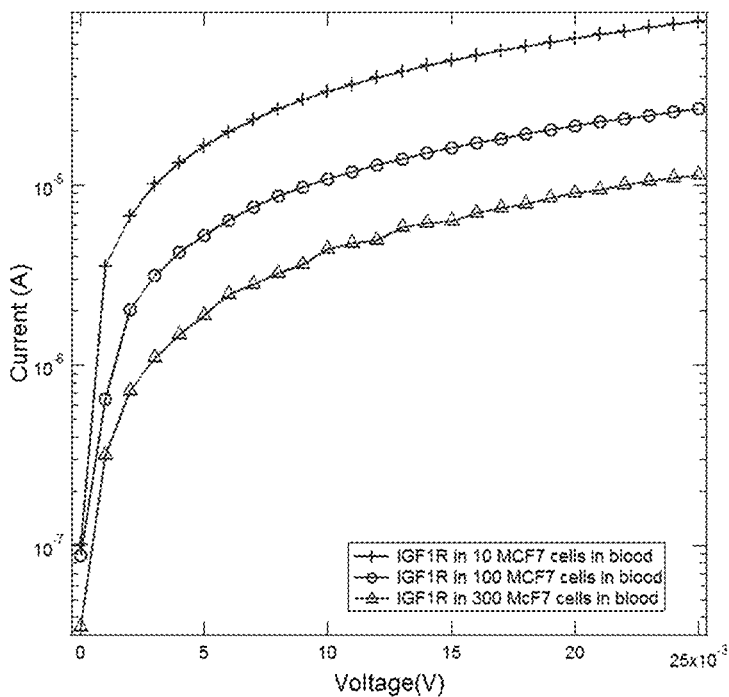
FIG. 8 is a chart illustrating I-V characteristics of an exemplary sensor consistent with the invention functionalized with IGF1R antibodies for blood samples with varying numbers of MCF7 cells.
Figure 9:
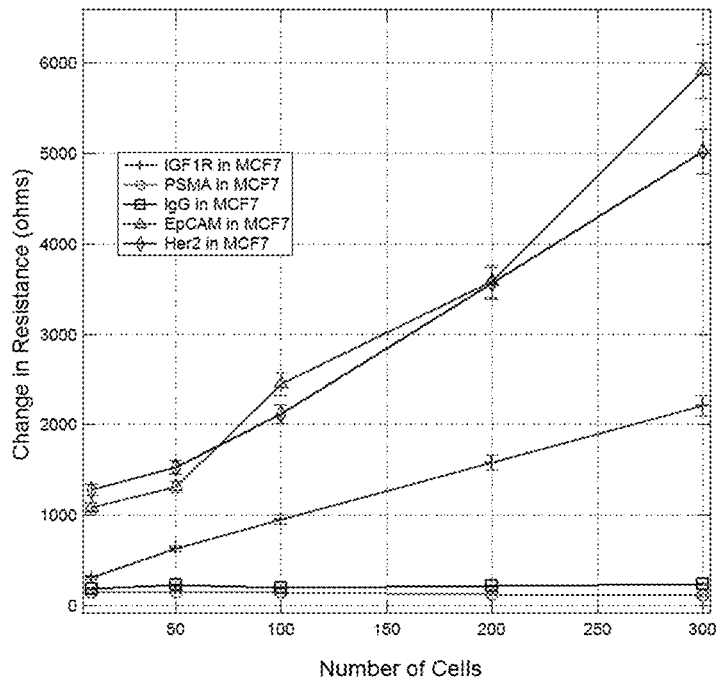
FIG. 9 is a chart illustrating a change of resistance in an exemplary sensor consistent with the invention as a number of MCF7 cells in blood samples when functionalized with several different antibodies.
Figure 10:
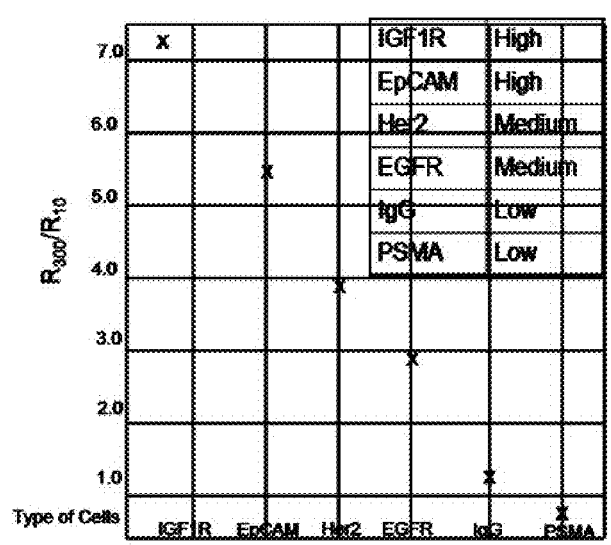
FIG. 10 is a chart illustrating overexpression ratios plotted as a function of antibody type, illustrating relatively high overexpression in IGF1R and EpCAM antibodies, medium overexpression in Her2 and EGFR antibodies, and low overexpression in IgG and PSMA antibodies.

The provisional application cross-referenced herein discusses test results performed with sensors fabricated in the manner disclosed herein. A portion of these results are illustrated in FIGS. 8-10. Detection and profiling of 10-300 MCF7 breast cancer cells in 5 µL aliquots of blood (the typical reported range for circulating tumor cells in the blood of patients with metastatic breast cancer) was performed. Incubation of blood spiked with cancer cells resulted in unambiguous decreases in sensor microjunction conductance, where pure blood resulted in higher conductance (lower resistance) of the microjunctions compared to blood spiked with cancer cells. The sensor was able to detect a minimum of 10 MCF7 cells in 5 µL of blood, as well as the maximum number of 300 MCF7 cells in blood for several different antibodies. FIG. 8, for example, illustrates the I-V characteristics of sensors functionalized with IGF1R antibodies using blood with 10-300 MCF7 cells, and shows a measurable decrease in conductivity with an increase in the number of MCF7 breast cancer cells in the blood.

FIG. 9 illustrates the change in resistance and conductance of sensors vs. the number of MCF7 cancer cells in a 5 µL blood sample for various antibodies, including IGF1R, EpCAM, and Her2, as well as non-specific IgG and PSMA antibodies, and shows that anti-IGF1R, anti-EpCAM, and anti-Her2 showed a measurable conductance change for MCF7 cells in blood as compared to the non-specific antibodies.

One potential way to scale cellular measurements is to determine a calibration curve between the cellular overexpression of a surface antigen and the change in electrical signal. In current clinical practice, diagnoses are mainly reported as the presence or absence of malignant cells in the specimen. The capability to quantify, profile, and stratify cancer cells would likely improve diagnosis. A critical issue when screening cancer cells is how to correlate the expression levels of tumor markers to the number of malignant cells in a given sample. Without this knowledge one could either measure high expression in relatively few cells or low expression in many cells.

One can define an overexpression ratio as $\Delta R^{Max\# \ of \ cells}/\Delta R^{Min\# \ of \ cells}$. This description is quite appropriate as this ratio increases with overexpression. One of the outcomes of results illustrated in FIG. 9 is that when one replots the data as overexpression ratios, one finds that the ratio of $\Delta R^{300}/\Delta R^{10}$ (IGF1R)=7.07, $\Delta R^{300}/\Delta R^{10}$ (EpCAM)=5.4, $\Delta R^{300}/\Delta R^{10}$ (Her2)=3.9, $\Delta R^{300}/\Delta R^{10}$ (EGFR)=2.9, $\Delta R^{300}/\Delta R^{10}$ (IgG)=1.27, and $\Delta R^{300}/\Delta R^{10}$ (PSMA)=0.77. This is shown in FIG. 10.

As can be seen in this figure, while the change in resistance of IGF1R in FIG. 9 was lower than EpCAM and Her2, the overexpression ratios were the highest for IGF1R. This shows that the definition of overexpression is indeed valid, and is in fact consistent with Western Blot analysis, which shows a similar overexpression of IGF1R in MCF7 cells compared to Her2. Further, the results also indicate specific numbers for EpCAM, EGFR and Her2 which are all valid surface markers for breast cancer. These overexpression ratios from 1.0 to 7.0 may also be assigned malignancy. A ratio of 1.0 may be considered benign or negative for that marker and 7.0 may be considered malignant or positive. Furthermore, based on these numbers one can scale the number of cells. From the aforementioned results, it is believed that plotting the number of cells against their overexpression ratios may give a linear change that can actually predict the number of cells in blood. Furthermore, by using more markers, one may be able to increase the accuracy of this technique.

It has also been found that, in some embodiments, it may also be desirable to alter the hydrophobicity or hydrophilicity of a biofunctional pad to alter the response characteristics of the biofunctional pad. It has been found, in particular, that a CNT thin film is typically hydrophobic in nature, and that the presence of a cellular target in a bodily source disposed on a biofunctional pad tends to decrease the conductivity of the CNT thin film in the biofunctional pad such that the conductivity of the thin film is inversely proportional to the presence of the cellular target in the bodily source. However, by treating the biofunctional pad to alter the physical structure of the CNT thin film, the hydrophilicity of the CNT thin film may be increased, and notably, the response of the biofunctional pad may be altered such that conductivity increases, rather than decreases, in response to the presence of a cellular target in a bodily source disposed on the biofunctional pad, such that the conductivity of the thin film is proportional to the presence of the cellular target in the bodily source.

Figure 11A:
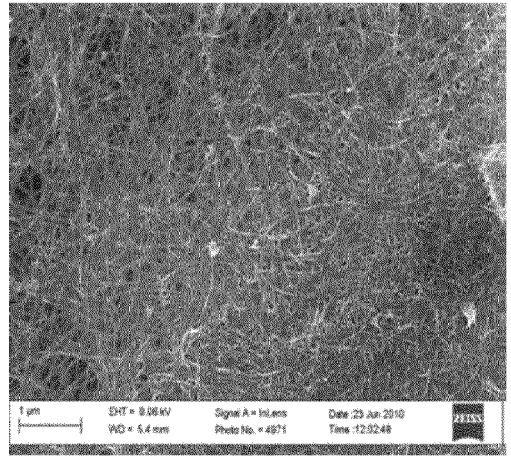
FIGS. 11A and 11B are scanning electronic microscope (SEM) image of a CNT thin film surface, uncoated (FIG. 11A) and coated with 10 µL of 5 µg/mL antibodies.

FIG. 11A, for example, illustrates an SEM image of the entangled nature of CNT's in a thin film. This type of entangled network presents ideal surface characteristics for cells to stick to such a surface. It has been found that the entangled nature of CNT's presents ideal surfaces for antibodies to stick to the surface even for non-covalent functionalization methods. The CNT surfaces show high degree of hydrophobicity due to the exposure of carbon nanotubes in a oxygen plasma during device patterning thereby creating rough surface. Adsorption of an antibody can decrease the surface energy thereby decoupling its surface wettability from bulk properties and enabling hydrophobicity. In addition, in some embodiments, the surface chemistry can be tailored with molecules such as silane to even create a superhydrophobic surface with high contact angles. Such surfaces are self-cleaning and therefore can enable variety of medical related devices.

Figure 11B:
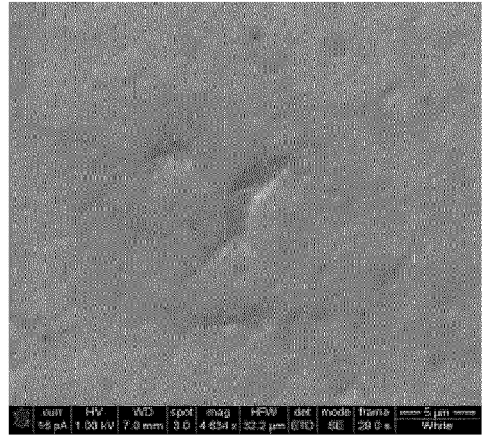

In one experimental implementation, for example, the electrical responses (I vs. Vds) of CNT thin film devices functionalized with specific antibodies were recorded in order to determine if different electrical signals were produced by antibody, blood, or blood with MCF-7 cells. FIG. 11B, for example, illustrates an SEM image of a CNT thin film functionalized with 10 µL of 5 µg/mL antibodies.

Figure 12A:
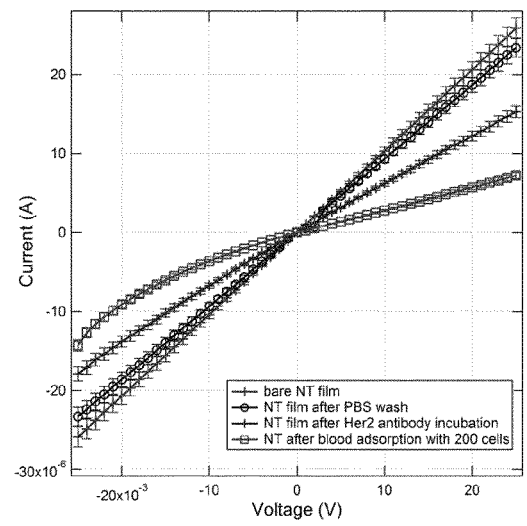
FIG. 12A is a representative I vs. Vds plots of experimental stages of an anti-Her2 functionalized CNT thin film transistor.
Figure 12B:
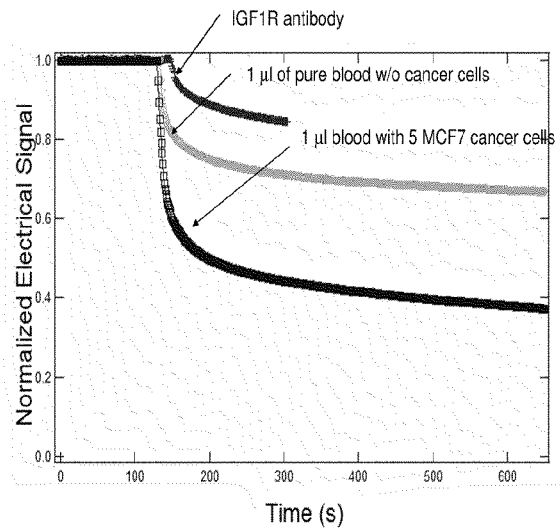
FIG. 12B is a plot of I vs. time comparisons for 1 µL of anti-IGF1R, 1 µL of pure blood, and 1 µL of blood spiked with 5 MCF-7 cells.

Upon adding biological components, noticeable changes in conductance were observed, as shown in a typical electrical measurement for an anti-HER2 coated device in FIG. 12A. The reduction in conductance was negligible for a phosphate buffered saline (PBS) wash. However, a 50% drop in the current of the device was observed after the adsorption of 5 µL of anti-HER2. After antibody adsorption, the addition of blood mixed with cancer cells resulted in an additional ~30% decrease in device conductance. This result is further observed from a real time current measurement (I vs. T), shown in FIG. 12B. Current decreased ~10% after adding antibodies, ~25% for a blood control sample and ~60% for blood mixed with cancer cells.

Figure 13:
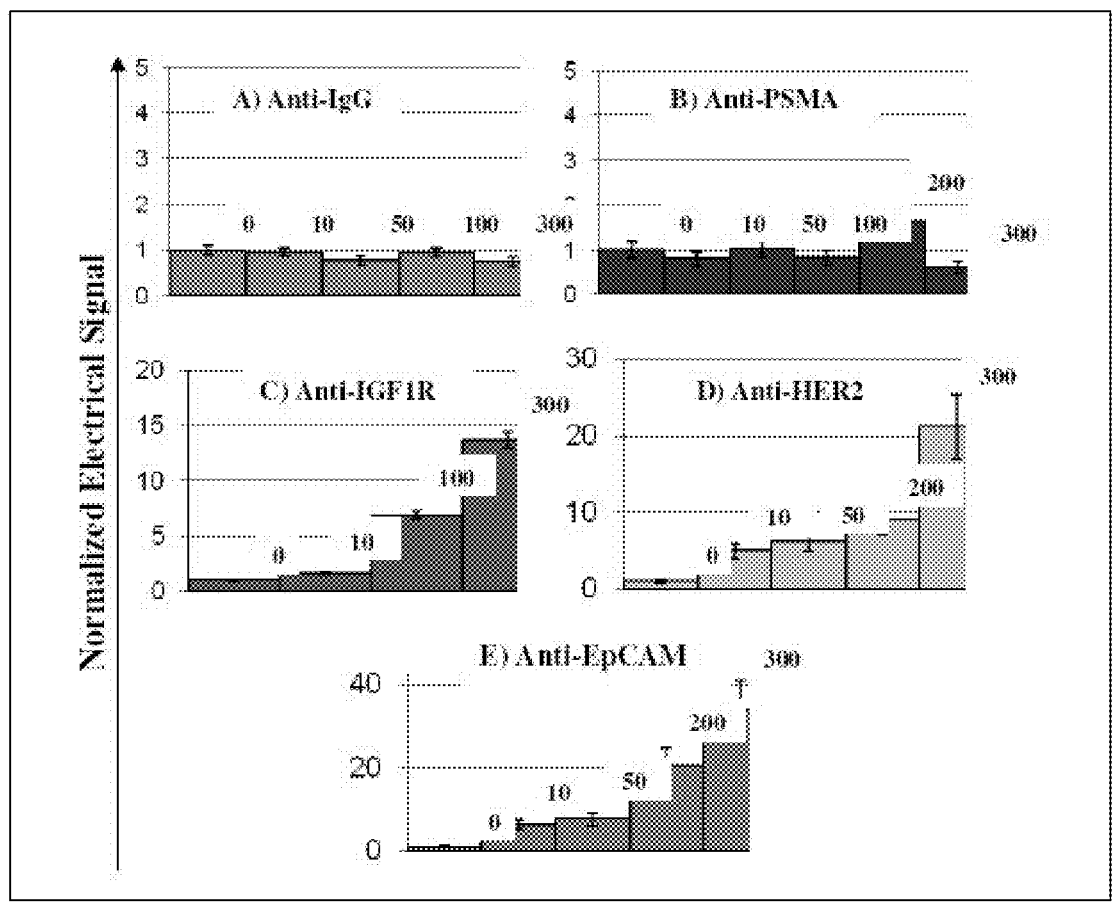
FIG. 13 is a plot of normalized electrical signals as a function of the number of MCF-7 cells for A) non-specific IgG antibody B) non-specific PSMA antibody C) specific IGF1R antibody D) specific HER2 antibody and E) specific EpCAM antibody functionalized CNT films.

The electrical behaviors of CNT thin films functionalized with specific (anti-IGF1R, anti-HER2 and anti-EpCAM) and non-specific (anti-IgG) or non-cognate (anti-PSMA) antibodies were measured in order to determine whether specific detection of MCF-7 cells was possible in a sample of unaltered blood. For an initial study, 5 µL of anti-IGF1R or anti-IgG were immobilized on the surface of the CNT networks followed by the addition of blood samples with a ramp of MCF-7 cell concentrations. FIG. 13 shows that devices printed with IgG experienced less than a ~10% change in conductivity while devices printed with IGF1R exhibited a ~60% drop in conductivity with increasing number of MCF-7 breast cancer cells in blood.

A summary of these specificity studies are presented in FIG. 13. Here it can be observed that for specific antibodies such as anti-IGF1R, anti-HER2 and anti-EpCAM, the electrical signal (resistance changes between current baseline and after adding MCF-7 cells with blood) increased as a function of increasing number of MCF-7 cells in blood samples. However, the same is not true for non-specific IgG and non-cognate PSMA. The electrical signatures remained the same despite the addition of blood mixed with MCF-7 cells. The specific interaction between antibodies and receptors on the cell surface may be defined in the form of a ratio called the overexpression ratio. The overexpression ratio is the ratio of change in electrical signal for the maximum number of cells spiked in blood (300 cells) to the change in electrical signal for the minimum number of cells in blood (10 cells). This relates to the specificity of the sensor. The ratio is highest for IGF1R (~7.0), EpCAM (~6.0), Her2 (~3.6) and IgG (~0.8). The ratios give some degree of specificity based on the binding of the antibodies to the receptors in cells. The number of binding sites for EpCAM and Her2 surface markers and their ratio have been shown in 9 different cancer cell lines using standard titration methods. For MCF7 cells the EpCAM expression was reported as 222.1 (713.7)×103 binding sites while Her2 expression was 25.2 (71.6)×103 binding sites respectively. Comparing these measurements to the overexpression ratios, the EpCAM over expression ratio was higher (~6.0) than the ratio for Her2 (~3.6) for MCF7 cells in blood, which suggests that the CNT-antibody array data gives similar results to standard titration methods for the number of binding events. In other words, it can be inferred that the change in electrical signal arises from the number of cooperative binding events happening on the surface of the device.

In another experimental implementation, I-V plots were recorded on 5 µL stabilized blood samples from three patients with metastatic breast cancer, the results of which are shown in Table I below:

TABLE 1

Molecular analysis of metastatic breast cancer patients

| Patient | ER | PR | Her2 | Veridex CTC, in 7.5 mL | CNT-mAb CTC, in 5 µl[†] |
|---------|----|----|------|------------------------|-------------------------|
| A | + | + | − | ND* | ~50 |
| B | + | + | − | 97 | ~50 |
| C | − | − | + | 1 | ~300 |

*deceased before Veridex available
[†]based on overexpression ratio

In this implementation, the CNT thin film devices were spotted with antibodies against IGF1R, HER2, EpCAM, EGFR, and nonspecific IgG, and tested with patient blood samples. The change in conductivity was almost 10-fold greater for specific antibodies over non-specific IgG.

Figure 14:
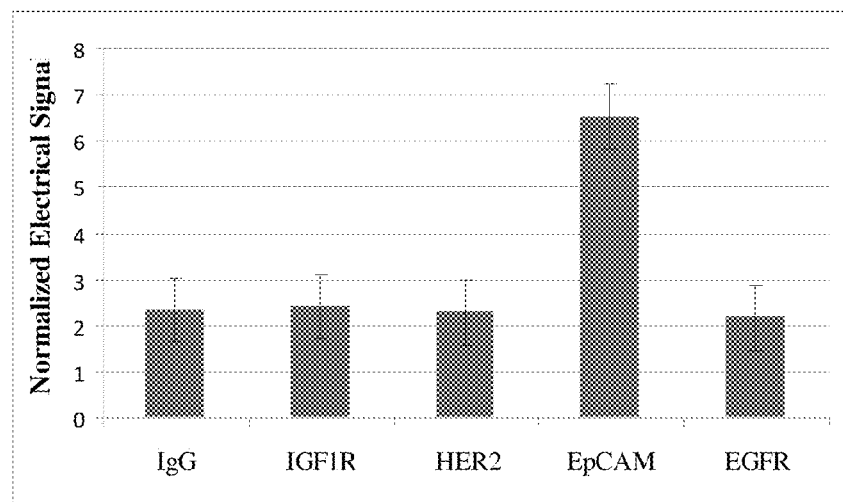
FIG. 14 illustrates changes in a normalized electrical signal for devices functionalized with IgG, IGF1R, Her2, EpCAM, and EGFR antibodies.

Electrical measurements equivalent to those performed from controlled blood samples were recorded for the three metastatic breast cancer patients. When I-V characteristics of patient C blood interacting with all the different antibodies was compared with immunohistochemical analysis done on Patient C, it was found that the cells were Her2-positive in both cases. Additionally, Veridex CellSearch analysis was performed for the patients. It was observed from both Patient B and C in Table 1 that when the cells were Her2-positive (Patient C, 1 cell detected), the Veridex gave low cell numbers compared to Her2-negative (Patient B, 97 cells detected). It is believed that the low cell numbers associated with Her2 status may indicate that EpCAM targeting alone cannot capture all CTC's in a blood sample. The surfaces of CTC's are heterogenous and therefore many different types of markers may be necessary for accurate capture, profiling, and enumeration of CTC's. FIG. 14 illustrates the changes in a normalized electrical signal for Patient B for devices functionalized with IgG, IGF1R, Her2, EpCAM, and EGFR antibodies.

In another experimental implementation, the surface interactions occurring in devices based on CNT thin film transistors were studied using liquid gated CNT FET's. The goal of these experiments was to identify the interactions between the CNT's and the antibody-receptor binding that lead to the charge carrier depletion or decrease in current. The transfer characteristics (I vs. Vg) of liquid gated transistors were monitored upon the addition of 1 µL of antibodies and 1 µL of 5 MCF-7 cells mixed with blood in order to identify the electrostatic interactions taking place between CNT's and the binding of surface receptors with antibodies. For these experiments, only one single concentration of MCF-7 cells (5 MCF-7 cells/µL) and blood was used. The transfer characteristics were recorded for devices functionalized with nonspecific IgG and anti-IGF1R antibodies as shown in FIGS. 15A and 15B (the anti-IgG and anti-IGF1R plots are above the MCF-7 plots in these figures). Distinct differences between the electrical characteristics of non-specific and specific interactions of MCF-7 surface receptors were observed. For a device printed with IGF1R antibodies, there was a shift in the threshold voltage (~250 mV), whereas devices printed with anti-IgG showed no distinguishable shift although conductance was reduced for negative gate voltage. The current decreased for both non-specific and specific antibodies in the negative gate voltage region. However, there was a shift in the gate voltage for the specific antibody in the positive side, suggesting that geometric deformations occur around the cellular interactions giving rise to a stress, leading to scattering sites on a CNT, and thus to reduced conductance. At the same time the device characteristic is modified only for negative gate voltages, leaving the transconductance in the positive gate voltage region unaffected.

For this latter experiment, an alternate device implementation may be used, where a localized liquid gate configuration modulates current in a conducting channel. The CNT FET's were scaled down to a smaller film area of ~0.008 mm$^2$ with only ~10-100 µm gap between patterned electrodes in order to observe any charge transfer and minimize the diffusive behavior of charged particles. Electrical currents were measured for specific and non-specific antibody-cells surface marker interactions. In addition, the relationship between electric current as a function of number of CTC's in a sample was explored. The change in signal level was related to the overexpression of targeted cell surface antigens.

As noted above, it may also be desirable in some embodiments to alter the surface of a CNT thin film to change the hydrophobicity or hydrophilicity of the surface. In one exemplary embodiment, for example, annealing may be performed, e.g., as discussed above in connection with block 64 of FIG. 4, but at a higher temperature than described in connection with this figure. It is believed that annealing at a higher temperature, e.g., about 200 to about 400 degrees Celsius, or about 300 degrees Celsius or higher, increases the hydrophilicity of a CNT thin film surface by "burning" the CNT's on the surface of the thin film, causing the CNT's to curl or curve, and effectively reducing the density of CNT's at the surface of the film. It is believed that by doing so, the continuity of the surface is interrupted, exposing holes or pits in the surface that receive liquid and thus increase the hydrophilicity of the surface. In one exemplary implementation, for example, it was found that a CNT thin film transforms from hydrophobic to hydrophilic at about 300 degrees Celsius.

It will be appreciated that altering the surface of a CNT thin film may be performed in a number of manners consistent with the invention. In addition to annealing a wafer after deposition of the thin film and electrodes, annealing may be performed at other points in the fabrication process, e.g. prior to electrode deposition. In addition, heat may be applied to the thin film in other manners, e.g., via infrared heating, etc. In addition, other surface treatments may be performed, including, for example, chemical treatment, oxygen plasma treatment, etc. In general, any treatment that lowers the density of CNT's on a thin film surface and increases hydrophilicity may be used consistent with the invention.

It has been found that altering the surface of a CNT thin film to render the surface hydrophilic causes the conductivity of a biofunctional pad functionalized with an antibody to increase in response to the presence of a biological target, which is opposite to the response of a CNT thin film with a hydrophobic surface. As such, in implementations where it is desirable to utilize a positive conductivity relationship with the presence of a biological target, treating the surface of the CNT thin film may be desirable.

In addition, the ability to selectively alter the surface of only some of the biofunctional pads on a wafer, e.g., as might be performed using infrared heating, provides the ability to provide both hydrophilic and hydrophobic biofunctional pads on the same wafer. In some embodiments, for example, the outputs of hydrophilic and hydrophobic biofunctional pads functionalized with the same antibody may be combined to increase the sensitivity and/or signal to noise ratio of a sensor, or to provide a reconfigurable functionalized surface for a sensor.

In still other embodiments, different surfaces may be combined with different antibodies to provide a more thorough analysis of the types of biological targets present in a bodily source. Different types of CTC's, for example, may exhibit different responses to different antibodies, so that not only the presence of a CTC in a blood sample, but the type of CTC, may be detected through the analysis of the conductivity of different biofunctional pads functionalized with different antibodies.

In an additional experimental implementation, a device comprising a CNT thin film with a hydrophobic surface was fabricated spanning between a pair of gold electrodes deposited on a glass substrate. 5 µL samples of ruby gold or gold nanoparticles of 3-5 nm were tested along with 5 µL samples of isolated white blood cells, isolated MCF7 cancer cells, blood and blood mixed with MCF7 cells, and the change in an electrical signal applied across the electrodes was measured for each sample. As shown in FIG. 16, the gold nanoparticles showed the smallest percentage change, followed by isolated white blood cells. Isolated MCF7 cells exhibited a larger percentage change; however, blood and blood mixed with MCF7 cells exhibited unique conductivity on the CNT surface, with the blood mixed with MCF7 cells exhibiting the highest conductivity.

Figure 17A:
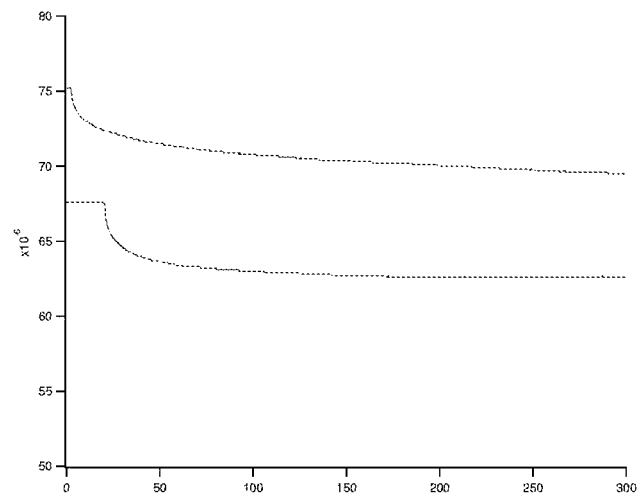
FIGS. 17A and 17B are plots of current vs. time for blood samples disposed on CNT thin films with hydrophobic (FIG. 17A) and hydrophilic (FIG. 17B) surfaces.
Figure 17B:
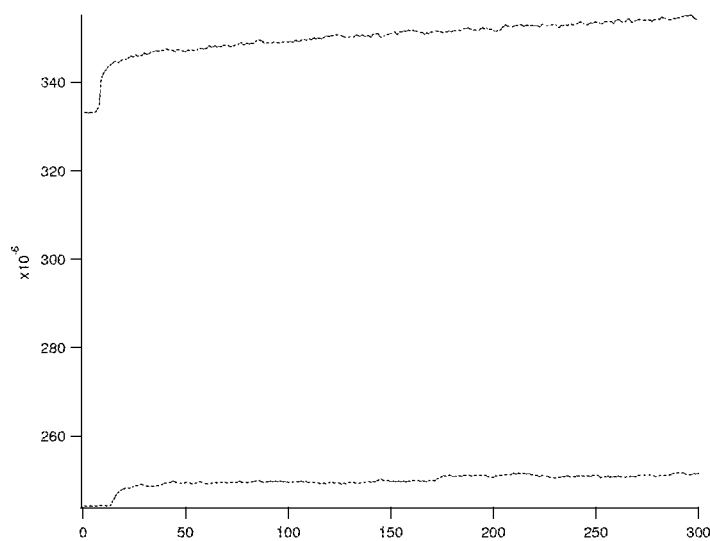

In addition, as shown in FIG. 17A, a measurement of current over time for the aforementioned device illustrates the decrease in conductivity over time seen in a hydrophobic CNT thin film upon which 5 μL of blood has been adsorbed. FIG. 17B, in contrast, illustrates a measurement of current over time for a similar device for which the CNT thin film is treated to render the surface hydrophilic, and with 5 μL of blood adsorbed thereon. In contrast with the hydrophobic surface, the plot of current vs. time for the hydrophilic surface exhibits an increase in conductivity over time. In each of FIGS. 17A and 17B, the plots of two blood samples are shown but are not normalized to one another, as the purpose of these figures is merely to illustrate the relative changes in conductivity that occur over time with CNT films having hydrophobic and hydrophilic surfaces.

Various additional modifications beyond those discussed herein will be apparent to one of ordinary skill in the art. Therefore, the invention lies in the claims hereinafter appended.

What is claimed is:

1. A device for detecting cellular targets in a bodily source, comprising:
   a substrate;
   at least one biofunctional pad comprising a thin film of carbon nanotubes (CNT's) disposed on the substrate and adapted to receive antibodies;
   a plurality of conductive contacts disposed on the substrate, the conductive contacts electrically coupled to the thin film;
   a layer of antibodies associated with a cellular target applied directly to a surface of the thin film of the biofunctional pad;
   at least a portion of the surface of the thin film being altered with a process in the formation of the device to provide the thin film with a hydrophilic surface so that with a layer of antibodies applied thereto, the conductivity of the biofunctional pad is proportional to the presence of the cellular target on the biofunctional pad;
   the plurality of conductive contacts configured for use in measuring a change in conductivity of the biofunctional pad when the bodily source is disposed on the biofunctional pad and in contact with the layer of antibodies for detecting the presence of the cellular target in the bodily source.

2. The device of claim 1, wherein the layer of antibodies is at least partially absorbed by the thin film.

3. The device of claim 1, wherein the cellular target comprises a cancer cell, and wherein the bodily source comprises a drop of blood.

4. The device of claim 1, wherein the thin film is rectangular in shape, and wherein the plurality of conductive contacts comprises first and second contacts disposed at and partially overlapping first and second corners of the thin film.

5. The device of claim 1, wherein the layer of antibodies is selected to target cellular receptors from the group consisting of IGF1R, Her2, EpCAM, and EGFR, and wherein the cellular target comprises a breast cancer cell.

6. The device of claim 1, wherein the thin film and the plurality of conductive contacts define a first sensor, the device further comprising a plurality of sensors disposed on the substrate, wherein each of the plurality of sensors respectively includes a thin film of CNT's and a plurality of conductive contacts electrically coupled to the respective thin film, and wherein the plurality of sensors are each adapted to receive a layer of antibodies selected from among a plurality of antibody types to detect different markers potentially associated with a cellular target.

7. The device of claim 1, wherein the bodily source functions as a polyelectric liquid gate for a transistor defined by the thin film and the plurality of contacts.

8. The device of claim 1, wherein at least another portion of the surface of a thin film of a biofunctional pad is hydrophobic, and wherein the conductivity of the another portion of a thin film is inversely proportional to the presence of the cellular target on the another portion of the surface of a thin film of the biofunctional pad.

9. The device of claim 1, wherein the portion of the surface is altered with a process that includes annealing the substrate to provide thin film with the hydrophilic surface after the plurality of conductive contacts is disposed thereon.

10. The device of claim 1 wherein at least a portion of the antibodies applied directly to a surface of the thin film are absorbed by the thin film of CNT's.

11. The device of claim 1, wherein the portion of the surface of the thin film is altered with a process that includes annealing the substrate to provide thin film with the hydrophilic surface after forming the thin film of CNT's.

12. The device of claim 11, wherein the substrate is annealed at a temperature of about 200 degrees Celsius to about 400 degrees Celsius.

13. The device of claim 11, wherein the substrate is annealed at a temperature of at least about 300 degrees Celsius.

14. The device of claim 1, wherein the portion of the surface of the thin film is altered with a process that includes the application of heat to the thin film to provide thin film with the hydrophilic surface.

15. The device of claim 1 wherein the portion of the surface of the thin film is altered with a process that includes at least one of chemical treatment or oxygen plasma treatment or infrared heating.

16. The device of claim 1 wherein the portion of the surface of the thin film is altered with a process that lowers the density of the carbon nanotubes on the thin film surface.

17. A device for detecting cellular targets in a bodily source, comprising:
   a substrate;
   at least one biofunctional pad comprising a thin film of carbon nanotubes (CNT's) disposed on the substrate and adapted to receive antibodies;
   a plurality of conductive contacts disposed on the substrate, the conductive contacts electrically coupled to the thin film;
   a layer of antibodies associated with a cellular target applied directly to a surface of the thin film of the biofunctional pad;
   at least a portion of the surface of the thin film being altered with a process in the formation of the device to provide the thin film with a hydrophilic surface and at least another portion of the surface of the thin film not being altered with the process so that, with a layer of antibodies applied to the biofunctional pad, the conductivities of the respective portions of the surface of the thin film are differently proportional with respect to each other in the presence of the cellular target on the biofunctional pad;
   the plurality of conductive contacts configured for use in measuring changes in conductivity of the biofunctional pad when the bodily source is disposed on the biofunctional pad and in contact with the layer of antibodies for detecting the presence of the cellular target in the bodily source.

18. The device of claim 17, wherein the portion of the surface is altered with a process that includes annealing the substrate to provide the thin film with the hydrophilic surface after the plurality of conductive contacts is disposed thereon.

19. The device of claim 17, wherein the portion of the surface of the thin film is altered with a process that includes annealing the substrate to provide the thin film with the hydrophilic surface after forming the thin film of CNT's.

20. The device of claim 17 wherein the portion of the surface of the thin film is altered with a process that includes at least one of chemical treatment or oxygen plasma treatment or infrared heating.

* * * * *